(12) United States Patent
Pizza et al.

(10) Patent No.: US 7,858,096 B2
(45) Date of Patent: *Dec. 28, 2010

(54) MUTANT FORMS OF MENINGOCOCCAL ADP-RIBOSYLATING TOXIN

(75) Inventors: Mariagrazia Pizza, Siena (IT); Vega Masignani, Siena (IT)

(73) Assignee: Novartis AC, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/526,125

(22) PCT Filed: Sep. 1, 2003

(86) PCT No.: PCT/IB03/04295

§ 371 (c)(1),
(2), (4) Date: Jun. 15, 2006

(87) PCT Pub. No.: WO2004/020634

PCT Pub. Date: Mar. 11, 2004

(65) Prior Publication Data

US 2006/0269563 A1     Nov. 30, 2006

(30) Foreign Application Priority Data

Aug. 30, 2002     (GB) ................ 0220205.9

(51) Int. Cl.
| | |
|---|---|
| A61K 39/02 | (2006.01) |
| A61K 39/00 | (2006.01) |
| C12N 9/22 | (2006.01) |
| C07H 21/04 | (2006.01) |
| A61K 38/00 | (2006.01) |
| A61K 38/04 | (2006.01) |
| C07K 14/00 | (2006.01) |

(52) U.S. Cl. ............. 424/190.1; 424/184.1; 435/199; 536/23.2; 530/300; 530/328; 530/329; 530/350

(58) Field of Classification Search ........... 424/190.1, 424/184.1; 435/199; 536/23.2; 530/300, 530/328, 329, 350

See application file for complete search history.

(56) References Cited

U.S. PATENT DOCUMENTS

| 7,115,730 B1 | 10/2006 | Pizza et al. | |
| 2006/0057155 A1* | 3/2006 | Masignani et al. | ....... 424/190.1 |

FOREIGN PATENT DOCUMENTS

| WO | WO 95/17211 | 6/1995 |
| WO | WO 02/079242 | * 10/2002 |

OTHER PUBLICATIONS

Domenighini et al., Common features of the NAD-binding and catlytic site of ADP-ribosylating toxins. Mol. Microbiol., 1994, vol. 14 (1): 41-50.*

Broun et al., Catalytic plasticity of fatty acid modification enzymes underlying chemical diversity of plant lipids. Science, 1998, vol. 282: 1315-1317.*

Kisselev L., Polypeptide release factors in prokaryotes and eukaryotes: same function, different structure. Structure, 2002, vol. 10: 8-9.*

Seffernick et al., Melamine deaminase and Atrazine chlorohydrolase: 98 percent identical but functionally different. J. Bacteriol.,2001, vol. 183 (8): 2405-2410.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Devos et al., Practical limits of function prediction. Proteins: Structure, Function, and Genetics. 2000, vol. 41: 98-107.*

Whisstock et al., Prediction of protein function from protein sequence. Q. Rev. Biophysics., 2003, vol. 36 (3): 307-340.*

Tettelin, H. et al. "Complete Genome Sequence of *Neisseria meningitidis* Serogroup B Strain MC58," Science, 287: 1809-1815 (2000).

Del Giudice, G. et al. "Genetically derived toxoids for use as vaccines and adjuvants," Vaccine, 17, Suppl 2: S44-S52 (1999).

Allured et al. (1986). "Structure of exotoxin A of *Pseudomonas aeruginosa* at 3.0-Angstrom resolution," *Proc. Natl. Acad. Sci.* USA, 83:1320-1324.

Antoine et al. (1993). "Evidence for a Catalytic Role of Glutamic Acid 129 in the NAD-glycohydrolase Activity of the Pertussis Toxin S1 Subunit," *The Journal of Biological Chemistry*, 268(32):24149-24155.

Barbieri et al. (1989). "Photolabeling of Glu-29 of the S-1 Subunit of Pertussis Toxin with NAD," *Infection and Immunity*, 57(11):3549-3554.

Burnette et al. (1988). "Pertusssi Toxin S1 Mutant with Reduced Enzyme Activity and a Conserved Protective Epitope," *Science*, 242(4875):72-74.

Carroll et al. (1984). "NAD binding site of diphtheria toxin: Identification of a residue within the nicotinamide subsite by photochemical modification with NAD," *Proc. Natl. Acad. Sci. USA*, 81:3307-3311.

Domenighini et al. (1994). "Common features of the NAD-binding and catalytic site of ADP-ribosylating toxins," *Molecular Microbiology*, 14(1):41-50.

Douglas et al, (1987). "Exotoxin A of *Pseudomonas aeruginosa*: Substitution of Glutamic Acid 553 with Aspartic Acid Drastically Reduces Toxicity and Enzymatic Activity," *Journal of Bacteriology*, 169(11):4967-4971.

Douglas et al. (1990). "*Pseudomonas aeruginosa* Exotoxin A: Alterations of Biological and Biochemical Properties Resulting from Mutation of Glutamic Acid 553 to Aspartic Acid," *Biochemistry*, 29(21):5043-5049.

(Continued)

*Primary Examiner*—Ganapathirama Raghu
(74) *Attorney, Agent, or Firm*—Amy Hessler; Otis Littlefield

(57) ABSTRACT

NMB1343 is an ADP-ribosylating toxin from *Neisseria meningitidis*. The invention provides a mutant toxin having a substitution at one or more of amino Glu-109, Glu-111 or Glu-120. The mutations(s) is/are preferably Glu to Asp. The protein of the invention preferably has reduced or eliminated ADP-ribosyltransferase and/or NAD-glycohydrolase activity relative to the wild-type protein.

14 Claims, 4 Drawing Sheets

OTHER PUBLICATIONS

Lobet et al. (1991). "Effect of Site-Directed Mutagenic Alterations on ADP-Ribosyltransferase Activity of the A Subunit of *Escherichia coli* Heat-Labile Enterotoxin," *Infection and Immunity*, 59(9):2870-2879.

Pizza et al. (1988). "Subunit S1 of pertussis toxin: Mapping of the regions essential for ADP-ribosyltransferase activity," *Proc. Natl. Acad. Sci.*, 85:7521-7525.

Rappuoli et al. (1991). "Structure and evolutionary aspects of ADP-ribosylating toxins," in *Bacterial Protein Toxins*. Alouf, J.E., Freer, J.H. (eds), London : Academic Press. p. 12.

Thanabalu et al. (1991). "Cloning, Sequencing, and Expression of a Gene Encoding a 100-Kilodalton Mosquitocidal Toxin from *Bacillus sphaericus* SSII-1," *Journal of Bacteriology*, 173(9):2776-2785.

Tsuji et al. (1991). "Glutamic acid-112 of the A subunit of heat-labile enterotoxin from enterotoxigenic *Escherichia coli* is important for ADP-ribosyltransferase activity," *FEBS*, 291(2):319-321.

Tweten et al. (1985). "Diphtheria Toxin: Effect of Substituting Aspartic Acid for Glutamic Acid 148 on ADP-Ribosyltransferase Activity," *The Journal of Biological Chemistry*, 260(19):10392-10394.

Wilson et al. (1990). "Active-Site Mutations of Diphtheria Toxin: Effects of Replacing Glutamic Acid-148 with Aspartic Acid, Gitamine, or Serine," *Biochemistry* 29:8643-8651.

Ala'Aldeen, D. et al. (1996). "Cloning, Sequencing, Characterization and Implications for Vaccine Design of the Novel Dihydrolipoyl Acetyltransferase of *Neisseria meningitidis*," *Journal of Medical Microbiology* 45:419-432.

Database Accession No. AX236858, last updated Sep. 26, 2001, located at <http://www.ncbi.nlm.nih.gov/entrez/viewer.fcgi?db=nuccore&id=15796444>, last visited on Jan. 26, 2009, 1 page.

Database EMBL Accession No. AE002482, last updated May 25, 2000, located at <http://www.ncbi.nlm.nih.gov/entrez/viewer.fcgi?db=nuccore&id=7226577>, last visited on Jan. 22, 2009, 8 pages.

Database EMBL Accession No. AX044032, last updated Nov. 24, 2000, located at <http://www.ncbi.nlm.nih.gov/entrez/viewer.fcgi?db=nuccore&id=11342916>, last visited on Jan. 23, 2009, 99 pages.

Database EMBL Accession No. CAA41592, last updated Sep. 23, 1991, located at <http://www.ncbi.nlm.nih.gov/entrez/viewer.fcgi?db=protein&id=48421>, last visited on Jan. 23, 2009, 2 pages.

Database EMBL Accession No. X77920, last updated May 14, 1999, located at <http://www.ncbi.nlm.nih.gov/entrez/viewer.fcgi?db=nuccore&id=534954>, last visited on Jan. 22, 2009, pages.

Database EMBL Accession No. X82637, last updated Jan. 7, 1997, located at <http://www.ncbi.nlm.nih.gov/entrez/viewer.fcgi?db=nuccore&id=577781>, last visited on Jan. 22, 2009, 3 pages.

Database SWALL Accession No. Q9JZ10, last updated Oct. 31, 2006, located at <http://www.ncbi.nlm.nih.gov/entrez/viewer.fcgi?db=protein&id=81784521>, last visited on Jan. 22, 2009, 2 pages.

Database EMBL Accession No. AAA81487 Database EMBL [Online] Dec. 4, 2000 Frazer, C.M. et al. (Apr. 20, 2000). "*N. meningitides* partial DNA sequence gnm_35 SEQ ID No. 35" retrieved from EBI Database accession No. AAA81487 XP002239408 & WO 00 22430 A (Chiron Corp.).

Database EMBL Accession No. AAY96654 Database EMBL [Online] Mason, H. S. and Arntzen, C.J. (Jun. 29, 2000): "Plant-optimized mutant V.cholera toxin subunit K63" retrieved from EBI Database accession No. AAY96654 XP002239411.

Freytag, LC. et al. (1999). "Bacterial Toxins as Mucosal Adjuvants," *Current Topics in Microbiology and Immunology* 236:215-236.

Glenn, G. et al. (1999). "Advances in Vaccine Delivery: Transcutaenous Immunisation," *Expert Opinion on Investigational Drugs* 8(6):797-805.

International Search Report mailed on Jan. 12, 2004, for PCT Application No. PCT/IB03/04295 filed on Sep. 1, 2003, 3 pages.

International Search Report mailed on Jul. 31, 2003, for PCT Application No. PCT/IB02/02080 filed on Mar. 28, 2002, 7 pages.

Krueger, K. et al. (1995). "The Family of Bacterial ADP-ribosylating Exotoxins," *Clinical Microbiology Reviews* 8:34-47.

Scharton-Kersten, T. et al. (2000). "Transcutaneous Immunization with Bacterial ADP-Ribosylating Exotoxins, Subunits, and Unrelated Adjuvants," *Infection and Immunity* 68(9): 5306-5313.

Seffernick, J. et al. (2001). "Melamine Deaminase and Atrazine Chlorohydrolase: 98 Percent Identical but Functionally Different," *Journal of Bacteriology* 186:2405-2410.

Wells, J. (1990). "Additivity of Mutational Effects in Proteins," *Biochemistry* 29:8509-8517.

Whisstock, J.C. et al. (Aug. 2003). "Prediction of Protein Function from Protein Sequence and Structure," *Quarterly Review of Biophysics* 36(3):307-340.

United States Office Action mailed on Dec. 11, 2009, for U.S. Appl. No. 10/472,681, filed Sep. 2, 2004, 15 pages.

United States Office Action mailed on Mar. 3, 2009, for U.S. Appl. No. 10/472,681, filed Sep. 2, 2004, 20 pages.

United States Office Action mailed on Jun. 16, 2008, for U.S. Appl. No. 10/472,681, filed Sep. 2, 2004, 17 pages.

United States Office Action mailed on Mar. 20, 2009, for U.S. Appl. No. 10/472,681, filed Sep. 2, 2004, 18 pages.

United States Office Action mailed on Mar. 28, 2007, for U.S. Appl. No. 10/472,681, filed Sep. 2, 2004, 20 pages.

Response to United States Office Action mailed on Sep. 28, 2007, for U.S. Appl. No. 10/472,681, filed Sep. 2, 2004, 15 pages.

Response to United States Office Action mailed on Dec. 15, 2008, for U.S. Appl. No. 10/472,681, filed Sep. 2, 2004, 15 pages.

Response to United States Office Action mailed on Aug. 17, 2009, for U.S. Appl. No. 10/472,681, filed Sep. 2, 2004, 13 pages.

Response to United States Office Action mailed on Apr. 12, 2010, 2009, for U.S. Appl. No. 10/472,681, filed Sep. 2, 2004, 11 pages.

United States Office Action mailed on Jul. 1, 2010, for U.S. Appl. No. 10/472,681, filed Sep. 2, 2004, 14 pages.

* cited by examiner

FIGURE 1
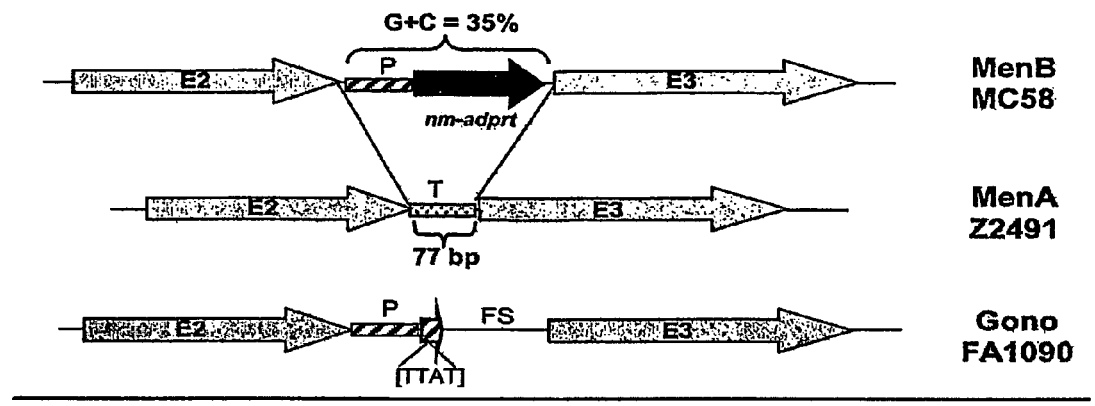
FIGURE 2
FIGURE 3
FIGURE 3A
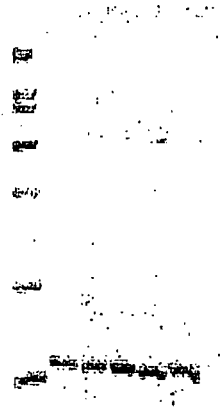
FIGURE 3B
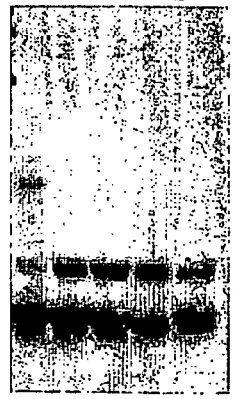

FIGURE 4
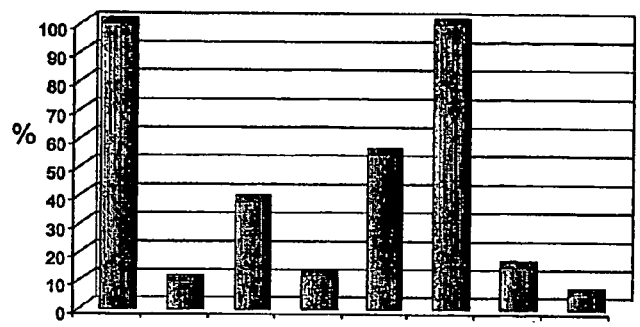
FIGURE 4A
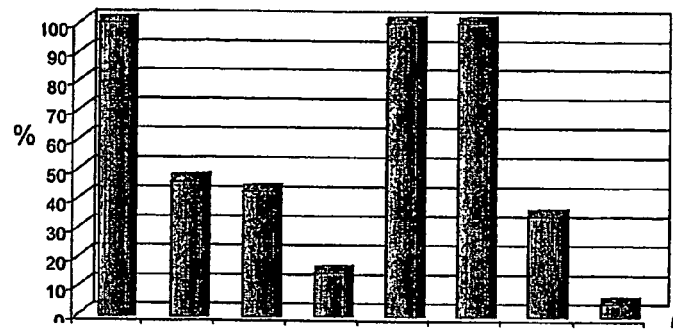
FIGURE 4B
FIGURE 6
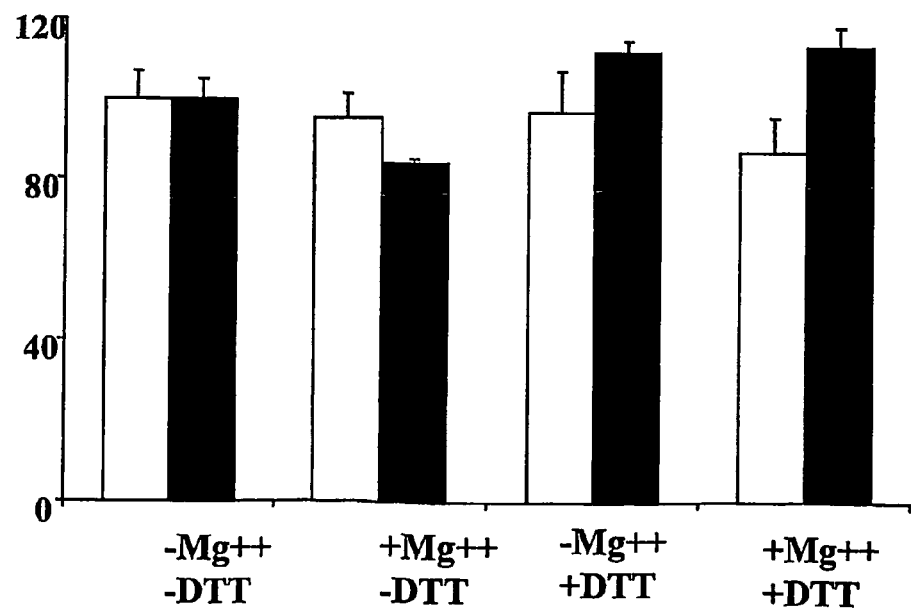

FIGURE 5

```
                    EEEE       HHHHHHHCEE CCCCC              EEE     HHHH    CCCCC           EEEEECCCHHHHHCCCCCCCC
            CT: KLWRRADSRPPDELKQSGGLMPRGQSE-----RGTQMINIYDNARGTQTGFVRHDDGYVSTSISLRSAHLVGQILSGHS
                    :=  :  : ::   :::              :::        : :: ::  :::::::      ::
NM-ADPRT:MGNFIEMRGISCQQDE--QNNGQLKPKGNKAEVAIRYDGKFKYDGKAATHGPSVKNAVTALQ---IETGL--YDGCMISWTDKEIAKKFATS---SGIE
           PHD:     EEE         CCCC EEEEEE                 EEE EEEEEEECCCCCCCCCCC               EEE  HHHHHHHH
      PsiPred: CCCCEEECCCCCCCCCC CCCCCCCCCCCCCC   CCCCCCCCEEEEEEEECCCCCCCCCCCCHHHHHHHHHHH  CCCC  CCCEEEBECCCCHHHHHHHHHHHHHH  CCCC
           HNN: EEEEEEE                          EEEEEE     HHHHHHHHHH    HHHHHHHHH           EEEE        HHHHHHHH
```

```
                    EEEEEE       CCEEEHHHHHCCCCCCCCC           CCCC EEEEE CCCEE       EE CC    HHHH
            CT: TYYIYVLATAPNMFNVNDVLGAYSPHPD---DLFGQYSIFEYEVEHPENPNKEVTIRAEDCGGIPYSQIYGMYRVHFGVLDEQLHRNRGYRDRYY
                   :::   :  ::  ::                :::                    :: :::
NM-ADPRT:NGYIYIVLRR--DLFGQYSIFEYEVEHPENPNKEVTIRAEDCGGIPYSQIYGMYRVHFGVLDEQLHRNRGYRDRYY
           PHD: EEEEEE          CC EEEEEEEE        CC  EEEEEEEEE          CCEEEEEEE      EEEEE CCCC           HHHHHHHH
      PsiPred: CCEEEEECC   CCCCCCEEEEECCCCC        CCCCCEEEEEECCCCC      CCCEEEEE      EEEEEE CCCCCCCCCCHHHHHHHHHHHCCC
           HNN: EEEEE                              EEEEEE                EEEEEE           HHHHHHHHHHH
```

MUTANT FORMS OF MENINGOCOCCAL ADP-RIBOSYLATING TOXIN

TECHNICAL FIELD

This invention is in the field of ADP-ribosylating bacterial toxins and their uses.

BACKGROUND ART

ADP-ribosylating bacterial exotoxins are widely known. Examples include diphtheria toxin (*Corynebacterium diphtheriae*), exotoxin A (*Pseudomonas aeruginosa*), cholera toxin (CT; *Vibrio cholerae*), heat-labile enterotoxin (LT; *E. coli*) and pertussis toxin (PT).

The toxins catalyse the transfer of an ADP-ribose unit from $NAD^+$ to a target protein. CT, for instance, transfers ADP-ribose to a specific arginine side chain of the α subunit of $G_S$, which blocks the ability of $G_s$ to hydrolyse GTP to GDP. This locks the protein in its 'active' form, so adenylate cyclase activity is permanently activated. Cellular cAMP levels rise, leading to the active transport of ions from the cell and the loss of water into the gut [1].

The toxins are typically divided into two functionally distinct domains—A and B. The A subunit is responsible for the toxic enzymatic activity, whereas the B subunit is responsible for cellular binding. The subunits might be domains on the same polypeptide chain, or might be separate polypeptide chains. The subunits may themselves be oligomers e.g. the A subunit of CT consists of $A_1$ and $A_2$ which are linked by a disulphide bond, and its B subunit is a homopentamer. Typically, initial contact with a target cell is mediated by the B subunit and then subunit A alone enters the cell.

Crystal structures [2] are known for LT [3], CT [4] and PT [5].

The toxins are typically immunogenic, and have been proposed for use in acellular vaccines. One problem, however, is that the proteins retain their toxic activity in the vaccines. To avoid this problem, site-directed mutagenesis of key active site residues has been used to remove toxic enzymatic activity whilst retaining immunogenicity [e.g. refs. 6 (CT and LT), 7 (PT), 8 etc.]. Current acellular whooping cough vaccines include a form of pertussis toxin with two amino acid substitutions ($Arg^9 \rightarrow Lys$ and $Glu^{129} \rightarrow Gly$; 'PT-9K/129G' [9]).

As well as their immunogenic properties, the toxins have been used as adjuvants. Parenteral adjuvanticity was first observed in 1972 [10] and mucosal adjuvanticity in 1984 [11]. It was surprisingly found in 1993 that the detoxified forms of the toxins retain adjuvanticity [12].

Although they display the same catalytic activity, the primary and secondary structures of ADP-ribosylating toxins are poorly conserved. Reference 13 discloses six ADP-ribosylating toxins with only a low level of sequence identity to toxins such as CT, LT and PT, from *Neisseria meningitidis, Streptomyces coelicolor, Mycoplasma pneumoniae, Salmonella typhimurium, Salmonella paratyphi*, and *Streptococcus pyogenes*. Mutants of the toxins are also disclosed.

It is an object of the invention to provide further mutant *N. meningitidis* toxins.

They are preferably prepared in substantially pure form (i.e. substantially free from host cell proteins).

The invention also provides the proteins of the invention for use as immunogens and/or as adjuvants and, in particular, as mucosal and/or parenteral adjuvants.

The invention also provides the use of proteins of the invention in the manufacture of a medicament for raising an immune response in an animal. The medicament is preferably an immunogenic composition (e.g. a vaccine), and may comprise, in addition to a protein of the invention, an antigen against which an enhanced immune response is to be raised. The medicament is preferably administered mucosally e.g. orally or intranasally.

The invention also provides immunogenic compositions (e.g. a vaccine) comprising a protein of the invention in admixture with a second antigen. It also provides a kit comprising a protein of the invention and a second antigen for simultaneous, separate or sequential administration. The second antigen is preferably one of the *N. meningitidis* proteins disclosed in references 15 to 21. The composition may comprise a third antigen, a fourth antigen, a fifth antigen etc., one or more of which may be selected from the *N. meningitidis* proteins disclosed in these seven references.

According to a further aspect, the invention provides antibody which binds to a protein of the invention. These may be polyclonal or monoclonal and may be produced by any suitable means. The antibody may include a detectable label. The antibody will bind to an epitope which includes one or more of amino acids Glu-109, Glu-111 or Glu-120.

According to a further aspect, the invention provides nucleic acid encoding the proteins of the invention. The invention includes nucleic acid comprising sequences complementary to those described above (e.g. for antisense or probing, or for use as primers).

Nucleic acid according to the invention can, of course, be prepared in many ways (e.g. by chemical synthesis, from genomic or cDNA libraries, from the organism itself etc.) and can take various forms (e.g. single stranded, double stranded, vectors, primers, probes etc.).

Nucleic acid according to the invention may be labelled e.g. with a radioactive or fluorescent label. This is particularly useful where the nucleic acid is to be used as a primer or probe e.g. in PCR, LCR or TMA.

In addition, the term "nucleic acid" includes DNA and RNA, and also their analogues, such as those containing modified backbones, and also peptide nucleic acids (PNA) etc.

According to a further aspect, the invention provides vectors comprising nucleic acid of the invention (e.g. cloning or expression vectors) and host cells transformed with such vectors.

DISCLOSURE OF THE INVENTION

Reference 13 discloses an ADP-ribosylating toxin from *N. meningitidis* (SEQ ID NO: 1 herein).

The present invention provides a mutant *Neisseria meningitidis* ADP-ribosylating protein, wherein the mutant has a substitution at one or more of amino acids Glu-109, Glu-111 or Glu-120. The mutation(s) is/are preferably Glu to Asp (e.g. SEQ ID $NO^s$: 2 to 4). The protein of the invention preferably has reduced or eliminated ADP-ribosyltransferase and/or NAD-glycohydrolase activity relative to the wild-type protein (e.g. relative to SEQ ID NO: 1).

The substitution(s) may be combined with further mutations elsewhere in the amino acid sequence e.g. substitutions, insertions, or deletions. Preferably, the amino acid sequences contains fewer than twenty mutations (e.g. 19, 18, 17, 16, 15, 14, 13, 12, 11, 10, 9, 8, 7, 6, 5, 4, 3, 2 or 1). Each mutation preferably involves a single amino acid.

The invention also provides a process for diminishing the ADP-ribosylating enzymatic activity of a *N. meningitidis* ADP-ribosylating protein, comprising mutating amino acid residue 109, 111 and/or 120 of said protein. This may conveniently be achieved by performing site-directed mutagenesis on nucleic acid encoding the toxin. The invention further provides a protein obtainable by this process.

Mutations may also be introduced to improve stability e.g. the insertion of disulphide bonds [14].

The protein of the invention is a "mutant" relative to a wild-type protein. The wild-type protein has ADP-ribosyltransferase and/or NAD-glycohydrolase activity and preferably comprises amino acid sequence SEQ ID NO: 1, or an amino acid sequence having sequence identity to SEQ ID NO: 1. The degree of sequence identity is preferably greater than 50% (e.g. 60%, 70%, 80%, 90%, 95%, 99% or more). These proteins include homologs, orthologs, allelic variants and functional mutants. Typically, 50% identity or more between two proteins is considered to be an indication of functional equivalence. Identity between proteins is preferably determined by the Smith-Waterman homology search algorithm as implemented in the MPSRCH program (Oxford Molecular), using an affine gap search with parameters gap open penalty=12 and gap extension penalty=1.

The invention further provides a protein comprising a fragment of a *Neisseria meningitidis* ADP-ribosylating protein, wherein (i) the fragment includes one or more of amino acids Glu-109, Glu-111 or Glu-120 from said ADP-ribosylating protein, and (ii) one or more of said amino acids Glu-109, Glu-111 or Glu-120 is substituted, preferably with an Asp. The fragment should comprise at least n consecutive amino acids from the toxin or mutant toxin and, depending on the particular sequence, n is 7 or more (e.g. 8, 10, 12, 14, 16, 18, 20, 30, 40, 50, 60, 70, 80, 90, 100 or more). Preferably the fragment comprises one or more epitopes from the toxin.

Proteins of the invention can, of course, be prepared by various means (e.g. recombinant expression, purification from native host, chemical synthesis etc.) and in various forms (e.g. native, fusions etc.).

According to a further aspect, the invention provides compositions comprising protein, antibody, and/or nucleic acid according to the invention. These compositions may be suitable as immunogenic compositions, for instance, or as diagnostic reagents, or as vaccines.

The invention also provides nucleic acid, protein, or antibody according to the invention for use as medicaments (e.g. vaccines) or diagnostic reagents. It also provides the use of nucleic acid, protein, or antibody of the invention in the manufacture of: (i) a medicament for treating or preventing bacterial infection; (ii) a diagnostic reagent for detecting the presence of bacteria or of antibodies raised against bacteria; and/or (iii) a reagent which can raise antibodies against bacteria. The bacterium is preferably *Neisseria meningitidis.*

The invention also provides a method of treating a patient, comprising administering a therapeutically effective amount of nucleic acid, protein, and/or antibody of the invention.

The proteins of the invention are particularly useful for treating meningococcal strains belonging to the ET-5 complex or to lineage III clusters. They are less useful for treating cluster A4 and ET-37 complex strains.

According to further aspects, the invention provides various processes.

A process for producing a protein of the invention is provided, comprising the step of culturing a host cell of to the invention under conditions which induce protein expression.

A process for producing protein or nucleic acid of the invention is provided, wherein the protein or nucleic acid is synthesised in part or in whole using chemical means.

A process for detecting a protein of the invention is provided, comprising the steps of: (a) contacting an antibody of the invention with a biological sample under conditions suitable for the formation of an antibody-antigen complexes; and (b) detecting said complexes.

Numbering of amino acids herein is relative to SEQ ID NO: 1. Where a sequence is part of a longer protein (e.g. a fusion protein) or where amino acids have been removed (e.g. C- or N-terminus truncations), the numbering may not, therefore, be absolute for the protein in question. If the N-terminus methionine is removed, for instance, residue Glu-109 will be residue 108 in absolute terms, but remains residue 109 relative to SEQ ID NO: 1.

A summary of standard techniques and procedures which may be employed to perform the invention (e.g. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art.

Such techniques are explained fully in the literature eg. Sambrook *Molecular Cloning; A Laboratory Manual, Third Edition* (2001); *DNA Cloning, Volumes I and II* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology series* (Academic Press, Inc.), especially volumes 154 & 155*; Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

DEFINITIONS

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g. a composition "comprising" X may consist exclusively of X or may include something additional e.g. X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a *staphylococcus* sequence is heterologous to a mouse host cell. A further example would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (eg. see U.S. Pat. No. 5,753,235).

Expression Systems

Nucleotide sequences can be expressed in a variety of different expression systems; for example those used with mammalian cells, baculoviruses, plants, bacteria, and yeast i. Mammalian Systems Mammalian expression systems are known in the art A mammalian promoter is any DNA sequence capable of binding mammalian RNA polymerase and initiating downstream (3') transcription of a coding sequence (eg. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100-200 bp upstream of the TATA box. An upstream promoter element determines the rate at which transcription is initiated and can act in either orientation [Sambrook et al.].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes (e.g., the murine metallotheionein gene) also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, as they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *PNAS USA* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2-215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Bimstiel et al. (1985) *Cell* 41:349; Proudfoot & Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminator/polyadenylation signals include those derived from SV40 [Sambrook et al].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers & Smith, *Texas Agricultural Experiment Station Bulletin No. 1555* (1987) (hereinafter "Summers & Smith").

Prior to inserting the DNA sequence encoding the protein into the baculovirus genome, the above described components, comprising a promoter, leader (if desired), coding sequence, and transcription termination sequence, are usually assembled into an intermediate transplacement construct (transfer vector). This may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extra-chromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 bp downstream from the ATT; see Luckow & Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene*, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l. Acad. Sci. USA*, 82:8404; mouse IL-3, (Miyajima et al., (1987) *Gene* 58:273; and human glucocerebrosidase, Martin et al. (1988) *DNA*, 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art (See Summers & Smith supra, Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al., eds) at 16.8 (Supp. 10, 1990); Summers & Smith, supra, Miller et al. (1989).

Recombinant baculovirus expression vectors have been developed for infection into several insect cells. For example, recombinant baculoviruses have been developed for, inter alia: *Aedes aeypti, Autographa californica, Bombyx mori, Drosophila melanogaster, Spodoptera frugiperda*, and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system cell culture technology is generally known to those skilled in the art See, eg. Summers & Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, etc. As appropriate, the product may be further purified, as required, so as to remove substantially any insect proteins which are also present in the medium, so as to provide a product which is at least substantially free of host debris, eg. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659, 122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in Jones & MacMillin, pages 21-52 of *Advanced Plant Physiology*, Malcolm B. Wilkins, ed., 1984 Pitman Publishing Limited. References that describe other metabolically-regulated genes: Sheen, *Plant Cell,* 2:1027-1038(1990); Maas et al., *EMBO J.* 9:3447-3452 (1990); Benkel & Hickey, *PNAS USA.* 84:1337-1339 (1987).

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a cell has been transformed. A general review of suitable markers, for example for the members of the grass family, is found in Wilmink & Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed & Maniatis, *Cell* 41:95-105, 1985.

The vector can be microinjected directly into plant cells by use of micropipettes to mechanically transfer the recombinant DNA. Crossway, *Mol. Gen. Genet*, 202:179-185, 1985. The genetic material may also be transferred into the plant cell by using polyethylene glycol, Krens, et al., *Nature*, 296, 72-74, 1982. Another method of introduction of nucleic acid segments is high velocity ballistic penetration by small particles with the nucleic acid either within the matrix of small beads or particles, or on the surface, Klein, et al., *Nature*, 327, 70-73, 1987 and Knudsen and Muller, 1991, *Planta*, 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *PNAS USA*, 79, 1859-1863, 1982.

The vector may also be introduced into the plant cells by electroporation. (Fromm et al., *PNAS USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Means for regeneration vary between plant species, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on genotype, and on the history of the culture. If these three variables are controlled then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *PNAS USA* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage, T7 RNA polymerase/promoter system is an example of a coupled promoter system [Studier et al. (1986) *J. Mol. Biol.* 189:113; Tabor et al. (1985) *PNAS USA* 82:1074]. In addition, a hybrid promoter can also be comprised of a bacteriophage promoter and an *E. coli* operator region (EP-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoff et al. (1989) *J. Gen. Microbiol.* 135:11], and *Chey* [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghlayeb et al. (1984) *EMBO J.* 3:2437] and the *E. coli* alkaline phosphatase signal sequence (phoA) [Oka et al. (1985) *PNAS USA* 82:7212]. As an additional example, the signal sequence of the alpha-amylase gene from various *Bacillus* strains can be used to secrete heterologous proteins from *B. subtilis* [Palva et al. (1982) *PNAS USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the

*Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described, components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *PNAS USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbiol. Lett.* 60:273; Palva et al. (1982) *PNAS USA* 79:5582; EP-A-0 036 259 and EP-A-0 063 953; WO 84/04541, *Bacillus*], [Miller et al. (1988) *PNAS USA.* 85:856; Wang et al. (1990) *J. Bacteriol.* 172:949, *Campylobacter*], [Cohen et al. (1973) *PNAS USA* 69:2110; Dower et al. (1988) *Nucleic Acids Res.* 16:6127; Kushner (1978) "An improved method for transformation of *Escherichia coli* with ColE1—derived plasmids. In *Genetic Engineering: Proceedings of the International Symposium on Genetic Engineering* (eds. Boyer & Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, so sequences encoding enzymes in the metabolic pathway provide particularly useful promoter sequences. Examples include alcohol dehydrogenase (EP-A-0 284 044), enolase, glucokinase, glucose-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *PNAS USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *PNAS USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase (EP-A-0012873; JPO 62,096,086) and A-factor (U.S. Pat. No. 4,588,684) genes. Alternatively, leaders of non-yeast origin, such as an interferon leader, exist that also provide for secretion in yeast (EP-A-0060057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) Gene 8:17-24], pC1/1 [Brake et al. (1984) PNAS USA 81:4642-4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually ~10 to ~150. A host containing a high copy number plasmid will preferably have at least about 10, and more preferably at least ~20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) PNAS USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast stains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol, Rev. 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans [Kurtz, et al. (1986) Mol. Cell. Biol. 6:142], Candida maltosa [Kunze, et al. (1985) J. Basic Microbiol. 25:141]. Hansenula polymorpha [Gleeson, et al. (1986) J. Gen. Microbiol. 132:3459; Roggenkamp et al. (1986) Mol. Gen. Genet. 202:302], Kluyveromyces fragilis [Das, et al. (1984) J. Bacteriol. 158:1165], Kluyveromyces lactis [De Louvencourt et al. (1983) J. Bacteriol. 154:737; Van den Berg et al. (1990) Bio/Technology 8:135], Pichia guillerimondii [Kunze et al. (1985) J. Basic Microbiol. 25:141], Pichia pastoris [Cregg, et al. (1985) Mol. Cell. Biol. 5:3376; U.S. Pat. Nos. 4,837,148 and 4,929,555], Saccharomyces cerevisiae [Hinnen et al. (1978) PNAS USA 75:1929; Ito et al. (1983) J. Bacteriol. 153:163]i Schizosaccharomyces pombe [Beach and Nurse (1981) Nature 300:706], and Yarrowia lipolytica [Davidow, et al. (1985) Curr. Genet. 10:380471 Gaillardin, et al. (1985) Curr. Genet. 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) Mol. Cell Biol. 6:142; Kunze et al. (1985) J. Basic Microbiol. 25:141; Candida]; [Gleeson et al. (1986) J. Gen. Microbiol. 132:3459; Roggenkamp et al. (1986) Mol. Gen. Genet. 202:302; Hansenula]; [Das et al. (1984) J. Bacteriol. 158:1165; De Louvencourt et al. (1983) J. Bacteriol. 154: 1165; Van den Berg et al. (1990) Bio/Technology 8:135; Kluyveromyces]; [Cregg et al. (1985) Mol Cell. Biol. 5:3376; Kunze et al. (1985) J. Basic Microbiol. 25:141; U.S. Pat. Nos. 4,837,148 and 4,929,555; Pichia]; [Hinnen et al. (1978) PNAS USA 75; 1929; Ito et al. (1983) J. Bacteriol. 153:163 Saccharomyces]; [Beach and Nurse (1981) Nature 300:706;

*Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying proteins of the invention.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 26 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (eg. hypoxanthine, aminopterin, thymidine medium, "HAT"). The resulting hybridomas are plated by limiting dilution, and are assayed for production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polygonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon their size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic, acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines according to the invention may either be prophylactic (ie. to prevent infection) or therapeutic (ie. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mich.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12 etc.), interferons (eg. γinterferon), macrophage colony stimulating factor (M-CSF), tumor necrosis factor TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (eg. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, their taxonomic group (eg. non-human primate, primate, etc.), the capacity of their immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection, either subcutaneously, intramuscularly, or transdermally/transcutaneously (eg. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be used [eg. Robinson & Torres (1997) *Seminars in Immunol* 9:271-283; Donnelly et al. (1997)*Annu Rev Immunol* 15:617-4648].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of coding sequence can be induced using endogenous mammalian or heterologous promoters. Expression of coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:5144; Kimura (1994) *Human Gene Therapy* 5:845-852; Connelly (1995) *Human Gene Therapy* 6:185-193; and Kaplitt (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses eg. MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J. Virol* 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J. Neurosci Res* 33:493-503; Baba (1993) *J Neurosurg* 79:729-735; Mann (1983) *Cell* 33:153; Cane (1984) *PNAS USA* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA inked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (ie. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary HSV vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC with accession numbers VR-977 and VR-260.

Also contemplated are alpha virus gene therapy vectors that can be employed in this invention. Preferred alpha virus vectors are Sindbis viruses vectors. Togaviruses, Semliki Forest virus (ATCC VR67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, *Nature* 339 (1989) 385 and Sabin (1973) *J. Biol. Standardization* 1:115; rhinovirus, for example ATCC VR-1110 and those described in Arnold (1990) *J Cell Biochem* 1401; pox viruses such as canary pox virus or vaccinia virus, for example ATCC VR-111 and ATCC VR-2010 and those described in Fisher-Hoch (1989) *PNAS USA* 86:317; Flexner (1989) *Ann NY Acad Sci* 569:86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *PNAS USA* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol* 66:2731; measles virus, for example ATCC VR67 and VR-1247 and those described in EP-4440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR469; Una virus, for example ATCC VR-374; Whataroa virus, for example ATCC VR-926; Y62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eukaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *PNAS USA* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *PNAS USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP40524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *PNAS USA* 84:7851; Plant (1989) *Anal Biochem* 176: 420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, polynucleotide compositions of the invention can be administered (1) directly to the subject; (2) delivered ex vivo, to cells derived from the subject; or (3) in vitro for expression of recombinant proteins. Subjects to be treated can be birds or mammals (including humans).

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene-mediated transfection, protoplast fusion, electroporation, encapsulation of polynucleotide(s) in liposomes, and direct microinjection of the DNA into nuclei, all well known in the art Polynucleotide and Polypeptide Pharmaceutical Compositions In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *PNAS USA* 84:7413-7416); mRNA (Malone (1989) *PNAS USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *PNAS USA* 75:4194-4198; WO90/11092 for a description of the synthesis of DOTAP (1,2-bis(oleoyloxy)-3-trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512-527; Szoka (1978) *PNAS USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *PNAS USA* 76:3348); Enoch & Strittmatter (1979) *PNAS USA* 76:145; Fraley (1980) *J. Biol. Chem.* (1980) 255: 10431; Szoka & Papahadjopoulos (1978) *PNAS USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI AII, AIV; CI, CII, CIII.

A lipoprotein can comprise more than one apoprotein. For example, naturally occurring chylomicrons comprises of A, B, C & E, over time these lipoproteins lose A and acquire C & E. VLDL comprises A, B, C & E apoproteins, LDL comprises apoprotein B; and HDL comprises apoproteins A, C, & E.

The amino acid of these apoproteins are known and are described in, for example, Breslow (1985) *Annu Rev. Biochem* 54:699; Law (1986) *Adv. Exp Med. Biol.* 151:162; Chen (1986) *J Biol Chem* 261:12918; Kane (1980) *PNAS USA* 77:2465; and Utermann (1984) *Hum Genet* 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in WO98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful, as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

Proteins of the invention can be used in immunoassays to detect antibody levels (or, conversely, antibodies of the invention can be used to detect protein levels). Immunoassays based on well defined, recombinant antigens can be developed to replace invasive diagnostics methods. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known;

examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 μg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 μg of yeast DNA, blotting for two hours, and hybridizing for 4-8 hours with a probe of $10^8$ cpm/μg. For a single-copy mammalian gene a conservative approach would start with 10 μg of DNA, blot overnight, and hybridize overnight in the presence of 10% dextran sulfate using a probe of greater than $10^8$ cpm/μg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%(G+C)]-0.6(\% \text{ formamide})-600/n-1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of hybridization increases (ie. stringency), it becomes less likely for hybridization to occur between strands that are non-homologous, and as a result, background decreases. If a radiolabeled probe is not completely homologous with the immobilized fragment (as is frequently the case in gene family and interspecies hybridization experiments), the hybridization temperature must be reduced, and background will increase. The temperature of washes affects the intensity of the hybridizing band and the degree of background in a similar way. The stringency of washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex that is stable enough to be detected Nucleic acid probes will hybridize to the nucleic acid of the invention (sense and/or antisense strands). Though many different nucleotide sequences will encode the amino acid sequence, the wild-type sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to a sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional sequence may also be helpful as a label to detect the formed duplex. For example, a non-complementary nucleotide sequence may be attached to the 5' end of the probe, with the remainder of the probe sequence being complementary to a bacterial sequence. Alternatively, non-complementary bases or longer sequences can be interspersed into the probe, provided that the probe sequence has sufficient complementarity with the a bacterial sequence in order to hybridize therewith and thereby form a duplex which can be detected.

The exact length and sequence of the probe will depend on the hybridization conditions (e.g. temperature, salt condition etc.). For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et ad [*PNAS USA* (1983) 80: 7461], or using commercially available automated oligonucleotide synthesizers.

The chemical nature of the probe can be selected according to preference. For certain applications, DNA or RNA are appropriate. For other applications, modifications may be incorporated eg. backbone modifications, such as phosphorothioates or methylphosphonates, can be used to increase in vivo half-life, alter RNA affinity, increase nuclease resistance etc. [eg. Agrawal & Iyer (1995) *Curr. Opin. Biotechnol* 6:12-19; Agrawal (1996) *TIBTECH* 14:376-387]; analogues such as PNAs may also be used [eg. see Corey (1997) *TIBTECH.* 15:224-229; Buchardt et al. (1993) *TIBTECH* 11:384-386].

Alternatively, the polymerase chain reaction (PCR) is another well-known means for detecting small amounts of target nucleic acid. The assay is described in Mullis et al. [*Meth. Enzymol.* (1987) 155:335-350] & U.S. Pat. Nos. 4,683,195 & 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired bacterial sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the bacterial sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

BRIEF DESCRIPTION OF DRAWINGS

FIG. 1 is a comparison of the nm-adprt locus in *N. meningitidis* serogroup B, *N. meningitidis* serogroup A and *N. gonorrhoeae.*

FIG. 2 is a western blot.

FIG. 3 shows purification of nm-adprt and mutants. In FIG. 3A the markers (left lane) are at 21, 31, 50, 66, 97, 116 and 200 kDa. In FIG. 3B the markers are 21, 31, 45, 66 and 97 kDa. To the right of the markers, the five lanes are wild-type, E109G, E111G, E120G and R7K.

FIG. 4 shows enzymatic activity (%) of nm-adprt and mutants. FIG. 4A shows ADP ribosyltrasferase and FIG. 4B shows NAD-glycohydrolase activity. From left to right, the eight columns are: wild-type, E109G, E111G, E120G, E109D, E111D, E120D and R7K.

FIG. 5 is an alignment of NM-ADPRT (SEQ ID NO: 1) with CT-A (SEQ ID NO: 13), also showing secondary structure.

FIG. 6 shows the effect of DTT and $Mg^{++}$ on enzymatic activity of NM-ADPRT. The values are percentages of control values for ADP-ribosyltransferase (□) and NAD-glycohydrolase (■) activity.

MODES FOR CARRYING OUT THE INVENTION

Figure 7:
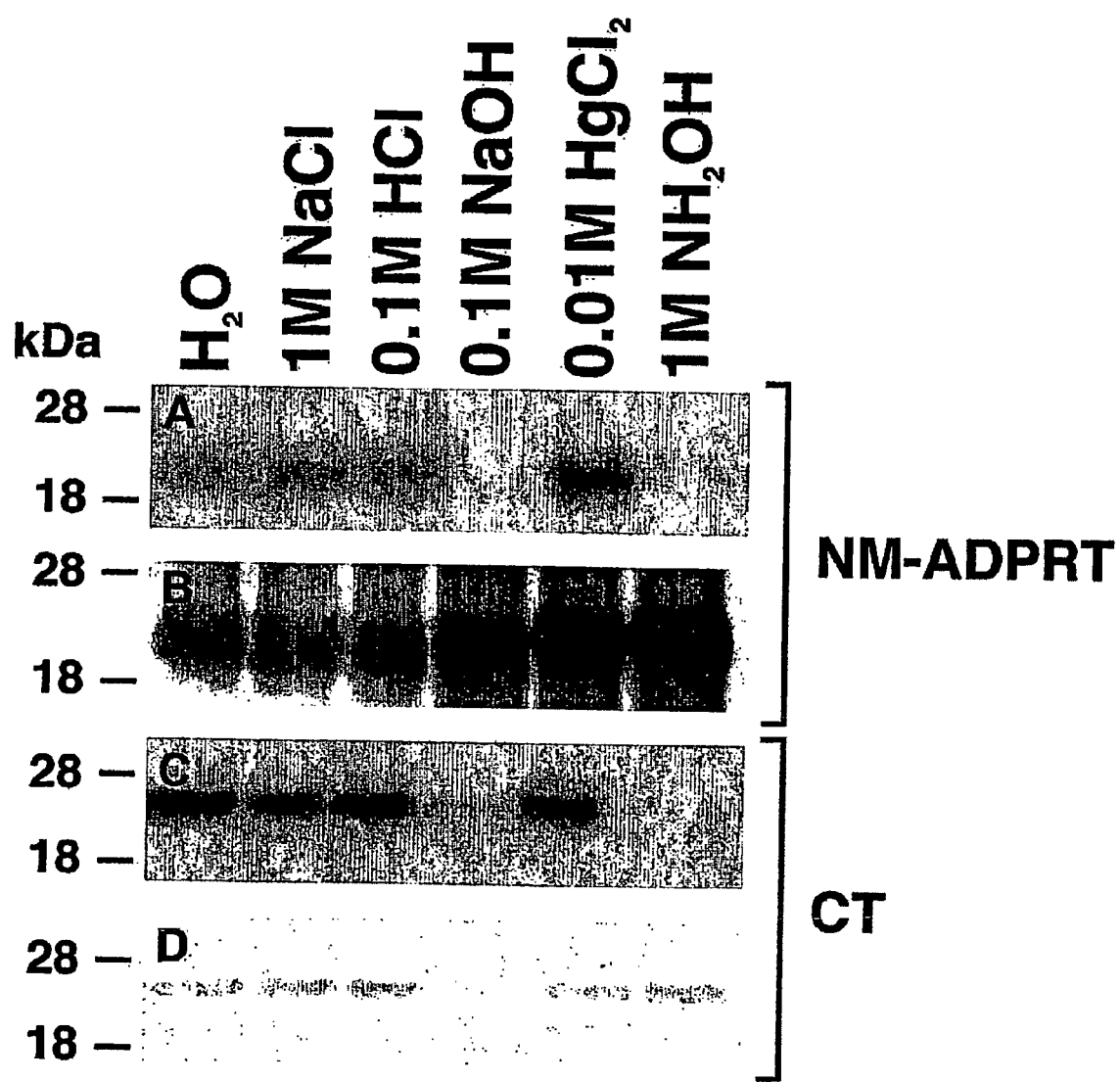
FIG. 7 shows the effect of various chemicals on NM-ADPRT.

Toxin Gene from *Neisseria meningitidis*, Serogroup B

Reference 13 discloses a protein with amino acid sequence <SEQ ID NO: 1> that was identified in *N. meningitidis* serogroup B strain MC58'. An alignment of the amino acid sequence with CT-A is shown in FIG. 5, including secondary structure prediction. Reference 13 also discloses that no corresponding gene was identified in *N. meningitidis* serogroup A (strain Z2491 [22]) or in *N. gonorrhoeae*. These absences have been investigated further.

In serogroup B strain MC58, the gene ('nm-adprt') is located within the operon of the pyruvate dehydrogenase multienzymatic complex, between the genes coding for the dihydrolipoamide acetyltransferase E2 and dihydrolipoamide dehydrogenase E3 components.

A putative promoter region was predicted upstream of nm-adprt, but no terminator sequence is present downstream, suggesting the possibility that nm-adprt and the gene for E3 might be co-transcribed in MC58 FIG. 3):

| SEQ ID NO | | |
|---|---|---|
| 6 | TATTCTTGGCGAAGCTGTTGAAAGACTTCCGCCGCATTACCTTATAAAATAAAACATCCC | |
| 5 | F L A K L L K D F R R I T L * | E2 |
| 6 | TCTCAAGCAGTCTGATAATGTTTGGATTGCTTGAGATTGATGAGTAATGGTGTTAAATTC | |
| — | | |

| SEQ ID NO | | |
|---|---|---|
| 6 | AACCTTTAAATTAATAACTTATGGGAAATTTCTTATATAGAGGCATTAGTTGCCAACAAG | |
| 1 |                 M  G  N  F  L  Y  R  G  I  S  C  Q  Q  D | nm-adprt |
| 6 | ATGAGCAAAATAATGGACAGTTAAAACCTAAAGGTAATAAAGCTGAAGTTGCAATTCGTT | |
| 1 | E  Q  N  N  G  Q  L  K  P  K  G  N  K  A  E  V  A  I  R  Y | |
| 6 | ATGATGGTAAGTTTAAATATGATGGTAAAGCTACACATGGTCCAAGTGTGAAGAATGCAG | |
| 1 | D  G  K  F  K  Y  D  G  K  A  T  H  G  P  S  V  K  N  A  V | |
| 6 | TTTACGCCCATCAAATTGAAACAGGTCTATATGACGGATGTTATATATCTACGACAACAG | |
| 1 | Y  A  H  Q  I  E  T  G  L  Y  D  G  C  Y  I  S  T  T  T  D | |
| 6 | ACAAGGAAATTGCCAAGAAATTTGCAACAAGTTCCGGCATCGAAAATGGCTATATATATG | |
| 1 | K  E  I  A  K  K  F  A  T  S  S  G  I  E  N  G  Y  I  Y  V | |
| 6 | TTTTAAATAGGGATTTGTTTGGTCAATATTCTATTTTTGAATATGAGGTTGAACATCCAG | |
| 1 | L  N  R  D  L  F  G  Q  Y  S  I  F  E  Y  E  V  E  H  P  E | |
| 6 | AAAACCCAAATGAGAAGGAAGTAACAATCAGAGCTGAAGATTGTGGCTGTATTCCTGAAG | |
| 1 | N  P  N  E  K  E  V  T  I  R  A  E  D  C  G  C  I  P  E  E | |
| 6 | AAGTGATTATTGCTAAAGAGTTGATAGAAATTAACTAAGTTGAAAGGTCAATATAATGGC | |
| — | M  A | E3 |

A gene coding for a putative receptor binding domain was not identified near nm-adprt, suggesting that it might belong to the "A-only" type of toxins, as is the case of the *Pseudomonas aeruginosa* exoenzyme S (ExoS) and other toxins such as C3 of *Clostridium botulinum*, EDIN of *Staphylococcus aureus* and the toxins of *Bacillus cereus* and of *Clostridium limosum*.

Analysis of the published serogroup A genome (Z2491 strain) [22] failed to identify an ORF equivalent to nm-adprt. A comparison of corresponding regions between MC58 and Z2491 genomes reveals that the insertion site of nm-adprt is directly upstream the ATG start codon of the E3 gene and comprises the open reading frame plus its. 5' upstream region, which contains a putative promoter region. The whole length of the inserted fragment in MC58 is 547 bp and is characterised by a GC content of 35%, surprisingly low with respect to the average GC composition of 51.5% calculated for *N. meningitidis*. In strain Z2491, this segment is replaced by a short stretch of 77 bp, which contains a stem loop sequence that very likely constitutes the terminator of the E2 gene:

| SEQ ID NO | | |
|---|---|---|
| 7 | TATTCCTGGCCAACCTGTTGAAAGACTTCCGCCGCATTACTCTGTAATCCGAGCATTTTC | E2 |
| 8 | F  L  A  N  L  L  K  D  F  R  R  I  T  L  * | |
| 7 | AGACGGCCTGAATAAAAAGGCCGTCTGAAAAAAGAAGTCCGAACATCATTCAGAAAGATT | |
| — | | |
| 7 | AGACATGAGCTTAGTTGAATTGAAAGTGCCCGACATTGGCGGTCACGAAAATGTAGATAT | |
| 9 | M  S  L  V  E  L  K  V  P  D  I  G  G  H  E  N  V  D  I | E3 |

Although no clear insertion site could be identified at the boundaries of the variable fragments in MC58 and Z2491, the low GC content of the segment and the fact that the gene is present in a subset of strains suggest that nm-adprt might have been acquired through a mechanism of horizontal transfer.

The analysis has been extended to the corresponding region in the genome of N. gonorrhoeae FA1090 [23]. The DNA segment is present, but a duplication of the tetranucleotide TTAT occurs 3 codons downstream the predicted ATG site, thus causing the premature interruption of the gene after only 8 codons:

affinity column. The column was extensively washed with 10 mM imidazole; 20 mM imidazole; 50 mM imidazole in the same buffer used for the pellet re-suspension and the NM-ADPRT protein was purified in a single step elution with 250 mM imidazole in the same buffer.

The samples (0.5 µg) were separated on SDS-PAGE 12.5% polyacrylamide gel (FIG. 3A). They were then transferred onto a nitrocellulose membrane overnight at 4° C. saturated in 3% skimmed milk, 0.1% Triton X100 in PBS and incubated for 1 hour at room temperature in a rabbit polyclonal antiserum diluted 1:10000. After two washes in 3% skimmed milk,

| SEQ ID NO | | |
|---|---|---|
| 10 | TATTCCTGGCGAACCTGTTGAAAGACTTCCGCCGCATTACCTTATAAAATAAAACATCCC | E2 |
| 11 | F L A N L L K D F R R I T L * | |
| 10 | TCTCAAGCAGTCTGATAATGTTTGGATTGCTTGAGATTGATGAGTGATGGTGTTAAATTC | |
| — | | |
| 10 | AAACTTTAAATTAATAACTTATGGGAAATTTCTTAT<u>TTAT</u>ATAGAGGCATTAGTTGCCAA | |
| 12 | M G N F L F I * | E3 |

FIG. 1 shows a comparison of the meningococcal A & B and the gonococcal DNA regions.

To assess the presence of nm-adprt in a higher number of strains, specific primers were used to amplify the gene from chromosomal DNA of 42 strains of N. meningitidis, representative of different serogroups and hypervirulent clusters, and in two strains of N. gonorrhoeae (Table I). In meningococcus the gene is always present in strains belonging to the ET-5 complex (12 strains) and lineage III (5 strains) clusters, and absent in cluster A4 (3 strains) and ET-37 complex (3 strains). When the gene is present, the amino acid sequence of the deduced polypeptide is perfectly conserved in all the meningococcal strains so far analysed. The strict conservation of the sequence in conjunction with the abnormal G+C content of the nm-adprt insertion suggest either a recent acquisition of the gene and/or a very high selective pressure in keeping the same protein sequence.

Western blot analysis of whole protein from MenB strains harbouring nm-adprt gene (lanes 2 to 6), one MenB strain lacking the gene (lane 7), and a gonococcal strain (lane 8) shows that NM-ADPRT is always expressed when its coding gene is present, without any variation in the expression level among different strains, and that the protein is not expressed at all in gonococcus, consistently with the sequence data (FIG. 2).

Protein Expression

The nm-adprt coding region devoid of the STOP codon was amplified by PCR from MC58 and cloned in the expression vector pET21b+, obtaining the plasmid pET-NM-ADPRT which encodes NM-ADPRT protein fused to a C-terminus hexa-histidine tag. This plasmid was introduced in E. coli strain BL21 (DE3). The transformed bacteria were grown at 37° C. to $OD_{550}$ of 0.6-0.8 in LB medium. Expression of recombinant protein was induced with 1 mM IPTG. Following induction, cells were collected by centrifugation at 8000 g for 15 minutes at 4° C. and the pellet was resuspended in 50 mM phosphate buffer pH 8.0 containing 300 mM NaCl and 10 mM imidazole. Samples were loaded on a metal-chelate 0.1% Triton X100 in PBS, the membrane was incubated for 1 hour with a POD-conjugated anti-rabbit antiserum diluted 1:10000. After four additional washes, the signal was developed and NM-ADPRT was detected at the same molecular weight of the recombinant protein (FIG. 3B).

Mutant Proteins

Based on homology with known toxins, catalytic residues were predicted. In reference 13 the arginine in position 7 was replaced with lysine using PCR-based site-directed mutagenesis and the glutamic acids in positions 109, 111 and 120 were similarly replaced by glycines.

Further mutants at amino acids 109, 111 and 120 have been prepared in which Asp is substituted for the native Glu (E109D, E111D, E120D; SEQ ID $NO^s$: 2 to 4). The mutant proteins were expressed and purified as described above.

Assay of Enzyme Activity

Purified mutant toxins were tested for both ADP-ribosylating and NAD-glycohydrolase activities.

The standard ADP-ribosyltransferase assay was carried out in 0.3 ml containing 50 mM potassium phosphate, pH 7.5, plus 20 mM or 75 mM agmatine and 0.1 mM [adenine-U-$^{14}$C]NAD (0.05 mCi).

After incubation at 30° C., duplicate samples (100 ml) were applied to 1 ml columns of Dowex AG 1-X2. [$^{14}$C]ADP-ribosylagmatine was eluted for radioassay with 5 ml of $H_2O$ and the radioactivity counted in a Packard mod counter.

NAD-glycohydrolase activity was evaluated with a radioactive assay using [carbonyl-$^{14}$C-NAD]. This assay was carried out in 50 mM potassium phosphate, pH 7.5, 0.1 mM [carbonyl-$^{14}$C]NAD (0.05 mCi) with and without 20 mM agmatine in a total volume of 0.3 ml. After incubation at 30° C. duplicate samples (100 ml) were applied to 1 ml column of Dowex AG 1-X2 and [$^{14}$C] nicotinamide was eluted with 5 ml $H_2O$ for liquid scintillation.

Results are shown in FIG. 4 (A: ADP ribosyltransferase; B: NAD-glycohydrolase). Mutants R7K, E109G, E111G, E120G and E120D showed significant reductions in enzymatic activity, with R7K, E120G and E120D being particularly marked.

Serum Bactericidal Assay

Antisera against NM-ADPRT and the mutant derivatives were obtained by immunisation of CD1 mice. 20 µg of each recombinant protein was given i.p. together with CFA for the first dose and IFA for the second (day 21) and the third (day 35) booster doses. Blood samples were taken on days 34 and 49. Immune sera were used in western blot and tested in a bactericidal assay against strain 2996.

SBA titres were as follows:

| Toxin | Titre |
|-------|-------|
| w. t. | <4 |
| R7K | 512 |
| E109G | <4 |
| E111G | 256 |
| E120G | 64 |

Thus titres induced by detoxified mutants were higher than those induced by the wild-type form. These data suggest that the mutations introduced could influence not only the enzymatic activity but also the in vivo stability of the toxin.

Enzymatic Activity in the Presence of DTT and $Mg^{++}$

Some bacterial ADP-ribosylating toxins need to be activated by sulfydryl agents and their activity is dependent on $Mg^{++}$.

ADP-ribosyltransferase (□) and NAD-glycohydrolase (■) activities were assayed with or without 20 mM DTT and/or 10 mM $MgCl_2$ as indicated in FIG. 6. NM-ADPRT (7 μg) was assayed in duplicate for 5 hours at 30° C. Data are means±S.D. (n=3).

In contrast with cholera [24] and pertussis toxins [25] that exhibited ADP-ribosyltransferase or NAD-glycohydrolase activity dependent on DTT and $Mg^{++}$ dependent, the rate of formation of ADP-ribosylagmatine by NM-ADPRT was independent of DTT and $Mg^{++}$. A slight activation (10%) was evidenced in the presence of DTT on the NAD-glycohydrolase activity.

Chemical Stability of NM-ADPRT Protein

ADP-ribose may be transferred to amino-acids like arginine, lysine, cysteine and glutamine. To identify which residue is modified in NM-ADPRT, $^{32}P$ labelled protein from an auto-ADP-ribosylation reaction [13] was incubated with various compounds.

After incubation at 37° C. for 1 hour with 10 μM [adenylate-$^{32}P$]NAD (10 μCi/assay), proteins were precipitated with trichloroacetic acid, resuspended in 50 μl of 1 M NaCl, 0.1 M HC, 0.1 M NaOH, 0.01 M $HgCl_2$, 1M $NH_2OH$ and incubated for 4 hour at 37° C. NM-ADPRT was precipitated in trichloroacetic acid, centrifuged, subjected to SDS-PAGE and then electroblotted to nitrocellulose, the radiolabelled bands were visualised by autoradiography (FIG. 7A). Western blotting of the transferred proteins is shown in FIG. 7B.

Radioactivity was released from the ADP-ribosylated NM-ADPRT by NaOH and $NH_2OH$, consistent with the presence of an ADP-ribosylarginine linkage [26]. CT that ADP-ribosylates itself at an arginine residue was used as positive control. Also in this case incubation with NaOH and $NH_2OH$ removed radioactivity (FIG. 7C).

It will be understood that the invention has been described by way of example only and modifications may be made whilst remaining within the scope and spirit of the invention.

TABLE I nm-adprt gene distribution in Neisseria, as determined by PCR experiments

| Strain | ET type | Classification | Year of Isolation | Country | Disease | nmb1343 gene | Source |
|---|---|---|---|---|---|---|---|
| MC58 | ET-5 | B:15:P1.7,16b | 1985 | UK | case | + | R. Moxon |
| BZ169 | ET-5 | B:15:P1.16 | 1985 | Netherlands | case | + | R. Moxon |
| 30/00 | ET-5 | B:15:P1.7,16 | 2000 | Norway | case | + | D. Caugant |
| BZ83 | ET-5 | B:15 | 1984 | Netherlands | case | + | R. Moxon |
| 72/00 | ET-5 | B:15:P1.7,13 | 2000 | Norway | case | + | D. Caugant |
| 39/99 | ET-5 | C:15:P1.7,16 | 1999 | Norway | case | + | D. Caugant |
| M4102 | ET-5 | B:ND | 1996 | USA | case | + | D. Caugant |
| 95330 | ET-5 | B:4:P1.15 | 1995 | Canada | case | + | D. Caugant |
| 220173I | ET-5 | NG:4:P1.15 | 1993 | Iceland | carrier | + | D. Caugant |
| 64/96 | ET-5 | NG:15:P1.7,16 | 1996 | Norway | carrier | + | D. Caugant |
| CU385 | ET-5 | B:4:P1.15 | 1980 | Cuba | case | + | D. Granoff |
| ISS1071 | ET-5 (?) | B:15:P1.7,16 | 2000 | Italy | case | + | P. Mastrantonio |
| L93/4286 | ET-37 | C | 1993 | UK | case | − | R. Moxon |
| 90/18311 | ET-37 | C:NT:P1.5 | 1990 | UK | case | − | R. Moxon |
| M986 | ET-37 | B:2a:P1.5,2 | 1963 | USA | case | − | D. Granoff |
| 961-5945 | Cluster A4 | B:2b:P1.21,16 | 1996 | Australia | case | − | G. Hogg |
| 312294 | Cluster A4 | C:2b:P1.5,2 | 1995 | UK | case | − | D. Caugant |
| 96217 | Cluster A4 | B:2b:P1.5,10 | 1996 | Canada | case | − | D. Caugant |
| BZ198 | Lineage 3 | B:NT | 1986 | Netherlands | case | + | R. Moxon |
| 980-2543 | Lineage 3 | B:NT:P1.4 | 1998 | Australia | case | + | G. Hogg |
| 394/98 | Lineage 3 | B:4:P1.4 | 1998 | New Zealand | case | + | E. Rosenqvist |
| ISS1106 | Lineage 3 (?) | B:4:P1.4 | 2000 | Italy | case | + | P. Mastrantonio |
| BZ133 | other | C:NT:-.- | 1977 | Netherlands | case | + | R. Moxon |
| F6124 | Subgroup III | A:-.- | 1988 | Chad | case | − | R. Moxon |
| 1000 | other | B:NT:P1.5 | 1988 | Russia | case | − | R. Moxon |
| NGE28 | other | B:4 | 1988 | Norway | carrier | − | R. Moxon |
| NGH38 | other | B:NT:P1.3 | 1988 | Norway | carrier | − | R. Moxon |
| BZ232 | other | B:NT:P1.2 | 1964 | Netherlands | case | − | R. Moxon |
| 2996 | other | B:2b:P1.5-1,2 | 1975 | UK | case | − | R. Moxon |

TABLE I-continued nm-adprt gene distribution in Neisseria, as determined by PCR experiments

| Strain | ET type | Classification | Year of Isolation | Country | Disease | nmb1343 gene | Source |
|---|---|---|---|---|---|---|---|
| 241175I | other | NG:21:P1.16 | 1993 | Iceland | carrier | + | D. Caugant |
| 171274I | other | NG:15:- | 1993 | Iceland | carrier | + | D. Caugant |
| 65/96 | other | B:4:P1.14 | 1996 | Norway | carrier | − | D. Caugant |
| 66/96 | other | B:17:P1.15 | 1996 | Norway | carrier | + | D. Caugant |
| 16060 | other | B:4:P1.14 | 1991 | Belgium | carrier | + | D. Caugant |
| C11 | — | C:16:P1.7a,1 | 1965 | Germany | — | − | R. Moxon |
| NMB | — | B:2b:P1.5,2 | 1968 | USA | case | − | D. Granoff |
| 8047 | — | B:2b:P1.2 | 1978 | USA | case | − | D. Granoff |
| S3446 | — | B:14:P1.23,14 | 1972 | USA | case | + | D. Granoff |
| ISS759 | — | C:2b:P1.2 | 1996 | Italy | case | − | P. Mastrantonio |
| ISS1001 | — | B:14:P1.13 | 1999 | Italy | case | + | P. Mastrantonio |
| ISS1113 | — | C:2a:P1.5 | 2000 | Italy | case | − | P. Mastrantonio |
| Ng F62 | Gonococcus | | | | | +* | |
| Ng SN4 | Gonococcus | | | | | +* | |

REFERENCES

The Contents of which are Hereby Incorporated in Full

[1] Rappuoli & Pizza (1991) Chapter 1 of *Sourcebook of Bacterial Protein Toxins* (Alouf & Freer, eds). ISBN 0-12-053078-3.
[2] Bazan & Koch-Nolte (1997) *Adv. Exp. Med. Biol.* 419:99-107.
[3] Sixma et al. (1991) *Nature* 351:371-377.
[4] Zhang et al. (1995) *J. Mol. Biol.* 251:563-573.
[5] Stein et al. (1994) *Structure* 2:45-57.
[6] International patent application WO93/13202.
[7] European patent applications 0306618, 0322533 and 0322115.
[8] Del Guidice & Rappuoli (1999) *Vaccine* 1999 17 Suppl 2:S44-52
[9] European patent 0396964.
[10] Northrup & Fauci (1972) *J. Infect. Dis.* 125:672ff.
[11] Elson & Ealding (1984) *J. Immunol.* 133:2892ff and 132:2736ff.
[12] International patent application WO95/17211.
[13] International patent application WO02/079242.
[14] van den Akker et al. (1997) *Protein Sci* 6:2644-2649.
[15] International patent application WO99/24578.
[16] International patent application WO99/36544.
[17] International patent application WO99/57280.
[18] Tettelin et al. (2000) *Science* 287:1809-1815.
[19] Pizza et al. (2000) *Science* 287:1816-1820.
[20] International patent application WO01/64920.
[21] International patent application WO01/64922.
[22] Parkhill et al. (2000) *Nature* 404:502-506.
[23] www.genome.ou.edu
[24] Moss et al. (1980) *J Biol Chem* 255:11085-7.
[25] Moss et al. (1983) *J Biol Chem* 258:11879-82.
[26] Cervantes-Laurean et al. (1993) *Biochemistry* 32:1528-34.

The invention claimed is:

1. A polypeptide having at least 90% sequence identity to SEQ ID NO: 1, wherein the polypeptide has a substitution at one or more of amino acids corresponding to Glu-109, Glu-111 or Glu-120 of SEQ ID NO: 1.

2. The polypeptide of claim 1, wherein the polypeptide has reduced or eliminated ADP ribosyltransferase or NAD-glycohydrolase activity relative to the wild-type enzyme, wherein the wild-type enzyme has amino acid sequence SEQ ID NO: 1.

3. The polypeptide of claim 1 or claim 2, wherein the substitution is Glu to Asp.

4. The polypeptide of claim 1, wherein the polypeptide comprises one of the amino acid sequences SEQ ID NO: 2, SEQ ID NO: 3 or SEQ ID NO: 4.

5. A polypeptide comprising a fragment of a polypeptide having at least 90% sequence identity to SEQ ID NO: 1, wherein (i) the fragment includes one or more of amino acids corresponding to Glu-109, Glu-111 or Glu-120 from said polypeptide, and (ii) one or more of said amino acids corresponding to Glu-109, Glu-111 or Glu-120 is substituted.

6. The polypeptide of claim 5, wherein the amino acid corresponding to Glu-109, Glu-111 or Glu-120 is substituted with Asp.

7. The polypeptide of claim 6 or claim 7, wherein the fragment comprises at least 7 consecutive amino acids from the polypeptide.

8. The polypeptide of claim 6 in admixture with a second antigen.

9. An immunogenic composition comprising the polypeptide of claim 1 in admixture with a second antigen.

10. A method of treating a patient, comprising administering a therapeutically effective amount of the polypeptide of any one of claims 1, 2, 4, 5, or 6.

11. The polypeptide of claim 1, wherein the polypeptide has at least 95% sequence identity to SEQ ID NO: 1.

12. The polypeptide of claim 1, wherein the polypeptide has at least 99% sequence identity to SEQ ID NO: 1.

13. The polypeptide of claim 5, wherein the polypeptide has at least 95% sequence identity to SEQ ID NO: 1.

14. The polypeptide of claim 5, wherein the polypeptide has at least 99% sequence identity to SEQ ID NO: 1.

* * * * *

SEQUENCE LISTING

```
<160> NUMBER OF SEQ ID NOS: 13

<210> SEQ ID NO 1
<211> LENGTH: 145
<212> TYPE: PRT
<213> ORGANISM: Neisseria meningitidis

<400> SEQUENCE: 1

Met Gly Asn Phe Leu Tyr Arg Gly Ile Ser Cys Gln Gln Asp Glu Gln
1               5                   10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95
```

Arg Asp Leu Phe Gly Gln Tyr Ser Ile Phe Glu Tyr Glu Val Glu His
                100                 105                 110

Pro Glu Asn Pro Asn Glu Lys Glu Val Thr Ile Arg Ala Glu Asp Cys
            115                 120                 125

Gly Cys Ile Pro Glu Glu Val Ile Ala Lys Glu Leu Ile Glu Ile
        130                 135                 140

Asn
145

<210> SEQ ID NO 2
<211> LENGTH: 145
<212> TYPE: PRT
<213> ORGANISM: Neisseria meningitidis

<400> SEQUENCE: 2

Met Gly Asn Phe Leu Tyr Arg Gly Ile Ser Cys Gln Gln Asp Glu Gln
1               5                   10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Asp Val Glu His
                100                 105                 110

Pro Glu Asn Pro Asn Glu Lys Glu Val Thr Ile Arg Ala Glu Asp Cys
            115                 120                 125

Gly Cys Ile Pro Glu Glu Val Ile Ala Lys Glu Leu Ile Glu Ile
        130                 135                 140

Asn
145

<210> SEQ ID NO 3
<211> LENGTH: 145
<212> TYPE: PRT
<213> ORGANISM: Neisseria meningitidis

<400> SEQUENCE: 3

Met Gly Asn Phe Leu Tyr Arg Gly Ile Ser Cys Gln Gln Asp Glu Gln
1               5                   10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Glu Val Asp His
                100                 105                 110

```
Pro Glu Asn Pro Asn Glu Lys Glu Val Thr Ile Arg Ala Glu Asp Cys
        115                 120                 125

Gly Cys Ile Pro Glu Glu Val Ile Ile Ala Lys Glu Leu Ile Glu Ile
    130                 135                 140

Asn
145

<210> SEQ ID NO 4
<211> LENGTH: 145
<212> TYPE: PRT
<213> ORGANISM: Neisseria meningitidis

<400> SEQUENCE: 4

Met Gly Asn Phe Leu Tyr Arg Gly Ile Ser Cys Gln Gln Asp Glu Gln
1               5                   10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45

Ser Val Lys Asn Ala Val Tyr Ala His Gln Ile Glu Thr Gly Leu Tyr
    50                  55                  60

Asp Gly Cys Tyr Ile Ser Thr Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                85                  90                  95

Arg Asp Leu Phe Gly Gln Tyr Ser Ile Phe Glu Tyr Glu Val Glu His
            100                 105                 110

Pro Glu Asn Pro Asn Glu Lys Asp Val Thr Ile Arg Ala Glu Asp Cys
        115                 120                 125

Gly Cys Ile Pro Glu Glu Val Ile Ile Ala Lys Glu Leu Ile Glu Ile
    130                 135                 140

Asn
145

<210> SEQ ID NO 5
<211> LENGTH: 14
<212> TYPE: PRT
<213> ORGANISM: Neisseria meningitidis, serogroup B

<400> SEQUENCE: 5

Phe Leu Ala Lys Leu Leu Lys Asp Phe Arg Arg Ile Thr Leu
1               5                   10

<210> SEQ ID NO 6
<211> LENGTH: 600
<212> TYPE: DNA
<213> ORGANISM: Neisseria meningitidis, serogroup B

<400> SEQUENCE: 6
tattcttggc gaagctgttg aaagacttcc gccgcattac cttataaaat aaaacatccc      60
tctcaagcag tctgataatg tttggattgc ttgagattga tgagtaatgg tgttaaattc     120
aacctttaaa ttaataactt atgggaaatt tcttatatag aggcattagt tgccaacaag     180
atgagcaaaa taatggacag ttaaaaccta aaggtaataa agctgaagtt gcaattcgtt     240
atgatggtaa gtttaaatat gatggtaaag ctacacatgg tccaagtgtg aagaatgcag     300
tttacgccca tcaaattgaa acaggtctat atgacggatg ttatatatct acgacaacag     360
```

```
acaaggaaat tgccaagaaa tttgcaacaa gttccggcat cgaaaatggc tatatatatg      420
ttttaaatag ggatttgttt ggtcaatatt ctattttga atatgaggtt gaacatccag       480
aaaacccaaa tgagaaggaa gtaacaatca gagctgaaga ttgtggctgt attcctgaag      540
aagtgattat tgctaaagag ttgatagaaa ttaactaagt tgaaaggtca atataatggc     600
```

<210> SEQ ID NO 7
<211> LENGTH: 180
<212> TYPE: DNA
<213> ORGANISM: Neisseria meningitidis, serogroup A

<400> SEQUENCE: 7

```
tattcctggc caacctgttg aaagacttcc gccgcattac tctgtaatcc gagcattttc      60
agacggcctg aataaaaagg ccgtctgaaa aagaagtcc gaacatcatt cagaaagatt      120
agacatgagc ttagttgaat tgaaagtgcc cgacattggc ggtcacgaaa atgtagatat     180
```

<210> SEQ ID NO 8
<211> LENGTH: 14
<212> TYPE: PRT
<213> ORGANISM: Neisseria meningitidis, serogroup A

<400> SEQUENCE: 8

```
Phe Leu Ala Asn Leu Leu Lys Asp Phe Arg Arg Ile Thr Leu
 1               5                  10
```

<210> SEQ ID NO 9
<211> LENGTH: 19
<212> TYPE: PRT
<213> ORGANISM: Neisseria meningitidis, serogroup A

<400> SEQUENCE: 9

```
Met Ser Leu Val Glu Leu Lys Val Pro Asp Ile Gly Gly His Glu Asn
 1               5                  10                  15

Val Asp Ile
```

<210> SEQ ID NO 10
<211> LENGTH: 180
<212> TYPE: DNA
<213> ORGANISM: Neisseria gonorrhoeae

<400> SEQUENCE: 10

```
tattcctggc gaacctgttg aaagacttcc gccgcattac cttataaaat aaacatccc      60 tctcaagcag tctgataatg tttggattgc ttgagattga tgagtgatgg tgttaaattc      120
aaactttaaa ttaataactt atgggaaatt tcttatttat atagaggcat tagttgccaa     180
```

<210> SEQ ID NO 11
<211> LENGTH: 14
<212> TYPE: PRT
<213> ORGANISM: Neisseria gonorrhoeae

<400> SEQUENCE: 11

```
Phe Leu Ala Asn Leu Leu Lys Asp Phe Arg Arg Ile Thr Leu
 1               5                  10
```

<210> SEQ ID NO 12
<211> LENGTH: 7
<212> TYPE: PRT
<213> ORGANISM: Neisseria gonorrhoeae

<400> SEQUENCE: 12

-continued

```
Met Gly Asn Phe Leu Phe Ile
1               5

<210> SEQ ID NO 13
<211> LENGTH: 147
<212> TYPE: PRT
<213> ORGANISM: Vibrio cholerae

<400> SEQUENCE: 13

Lys Leu Tyr Arg Ala Asp Ser Arg Pro Pro Asp Glu Ile Lys Gln Ser
1               5                   10                  15

Gly Gly Leu Met Pro Arg Gly Gln Ser Glu Tyr Phe Asp Arg Gly Thr
            20                  25                  30

Gln Met Asn Ile Asn Leu Tyr Asp His Ala Arg Gly Thr Gln Thr Gly
        35                  40                  45

Phe Val Arg His Asp Asp Gly Tyr Val Ser Thr Ser Ile Ser Leu Arg
    50                  55                  60

Ser Ala His Leu Val Gly Gln Thr Ile Leu Ser Gly His Ser Thr Tyr
65                  70                  75                  80

Tyr Ile Tyr Val Ile Ala Thr Ala Pro Asn Met Phe Asn Val Asn Asp
                85                  90                  95

Val Leu Gly Ala Tyr Ser Pro His Pro Asp Glu Gln Glu Val Ser Ala
            100                 105                 110

Leu Gly Gly Ile Pro Tyr Ser Gln Ile Tyr Gly Trp Tyr Arg Val His
        115                 120                 125

Phe Gly Val Leu Asp Glu Gln Leu His Arg Asn Arg Gly Tyr Arg Asp
    130                 135                 140

Arg Tyr Tyr
145
```